United States Patent [19]

Tesoro et al.

[11] Patent Number: 4,778,727
[45] Date of Patent: Oct. 18, 1988

[54] SILANE COUPLING AGENTS POLYIMIDE-MINERAL OXIDE COMPOSITES

[75] Inventors: Giuliana C. Tesoro, Dobbs Ferry, N.Y.; Donald R. Uhlmann, Newton, Mass.; Giovindasamy P. Rajendran, Brooklyn, N.Y.; Chan E. Park, Cambridge, Mass.

[73] Assignee: Massachusetts Institute of Technology, Cambridge, Mass.

[21] Appl. No.: 41,559

[22] Filed: Apr. 23, 1987

Related U.S. Application Data

[62] Division of Ser. No. 822,366, Jan. 24, 1986, abandoned.

[51] Int. Cl.[4] .................. B32B 9/04; B32B 15/08; B32B 27/08
[52] U.S. Cl. ............................. 428/448; 428/457; 428/473.5; 428/901
[58] Field of Search ................ 428/447, 448, 473.5, 428/901, 457; 525/125; 548/406

[56] References Cited

U.S. PATENT DOCUMENTS 3,981,913  8/1975  Kim .................................. 548/406
4,161,477  7/1979  Long et al. ....................... 528/125 X

OTHER PUBLICATIONS

Greenblatt et al., Chem. Abstracts, vol. 102:205011a, 1985, p. 50.

Primary Examiner—Thomas J. Herbert
Attorney, Agent, or Firm—Paul J. Cook

[57] ABSTRACT

An adhesion promoter for polyimide is provided having the formula:

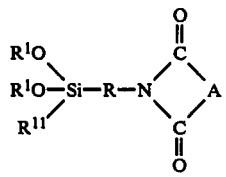

wherein A is

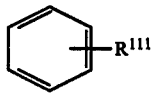

or

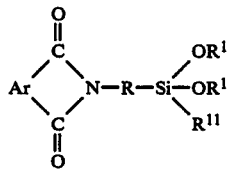

Ar is an aromatic group, $R^1$ is lower alkyl, $R^{11}$ is $OR^1$ or lower alkyl, $R^{111}$ is hydrogen or lower alkyl.

9 Claims, No Drawings

SILANE COUPLING AGENTS POLYIMIDE-MINERAL OXIDE COMPOSITES

This is a divisional of co-pending application Ser. No. 822,366, filed on Jan. 24, 1986, now abandoned.

BACKGROUND OF THE INVENTION

The present invention relates to novel organofunctional imidesilane coupling agents which exhibit exceptionally high thermal stability and outstanding coupling effectiveness in composites consisting of a polyimide resin matrix and a mineral oxide substrate. The invention also relates to the methods of synthesizing, isolating and employing the compounds in polyimide-mineral oxide composites.

In producing integrated circuits, use is made frequently of a silica substrate to which is adhered a patterned polyimide wash to provide dielectric isolation. Frequently, these circuits are formed at elevated temperatures of up to about 300° C. or higher which requires that adhesion promoters utilized in the circuit formation provide strong bonding and are thermally stable. Extensive research has been carried out to develop silane coupling agents for high temperature resins. For example, numerous reactive organofunctional aromatic silanes have been evaluated [e.g., Pleuddemann, Proceedings, 22nd Annual Meeting of the Reinforced Plastics Division of the Society of the Plastics Industry, Sec. 9-A, p. 1 (1967)] and a ranking of thermal stability has been proposed. More recently, ethylene bridged aromatic silanes have been suggested as high temperature coupling agents [B. Arkles and W. Peterson, Proceedings, 35th Annual Technical Conference. Reinforced Plastics Composites Institute, SPI (1980)]. However, known compounds have not exhibited the balance of properties required in commercial applications of composites comprising polyimide resins and films and a mineral oxide substrate. These properties include solubility, reactivity, interpenetrating compatibility of the polymer formed at the interface with the polyimide and the high adhesive strength at the interface retained upon exposure of the composite to elevated temperature.

Attempts have been made to incorporate amino-functional silanes in polyimide resins in order to improve the adhesive strength of the modified polymers in composites without pretreatment of the substrate with adhesion promoters. Such "integral mix" coupling approaches, in which coupling agents were not isolated, characterized and separately applied, disclosed, for example, in German Offenlegungschrift No. 2,838,874 and in U.S. Pat. No. 4,161,477, have many limitations and do not represent a solution to the problem of thermally stable coupling agents for polyimide composites.

It would be desirable to provide coupling agents for effecting adhesion between a polyimide and a mineral oxide substrate which effect a strong bond and which are thermally stable. Such coupling agents would facilitate the production of the composite products, particularly integrated circuits.

SUMMARY OF THE INVENTION

The compounds of the present invention can be utilized in diverse applications of polyimides; and furthermore, their structure can be tailored to meet the most exacting requirements of functionality, solubility, compatibility, reactivity and thermal stability.

The compounds of this invention are prepared by reacting an amino-functional silane of Formula I $$H_2N-R-Si\begin{array}{c}OR^1\\OR^1\\R^{11}\end{array} \qquad \text{Formula I}$$

where
R is a divalent radical comprising more than two carbon atoms, which can be aliphatic, such as alkylene, aubstituted alkylene; aromatic, such as phenylene or naphthylene; or alkyl aromatic, and can contain heteroatoms as substituents or as part of the chain,
$R^1$ is lower alkyl from 1 to 6 carbon atoms
$R^{11}$ is $-OR^1$ or lower alkyl from 1 to 6 carbon atoms
with
(a) an aromatic anhydride of Formula II Formula II where $R^{111}$ is hydrogen or alkyl from 1 to 6 carbon atoms
(b) an aromatic dianhydride of Formula III Formula III where Ar is an aromatic group, examples of which include:

(c) a dialkyl ester of an aromatic o-dicarboxylic acid of Formula IV

Formula IV where $R^{iv}$ is lower alkyl from 1 to 6 carbon atoms and $R^v$ is lower alkoxy from 1 to 6 carbon atoms or halide such as chlorine.

(d) an alkyl ester of an aromatic, 0,0'-tetracarboxylic acid of Formula V

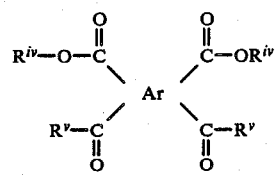

Formula V where $R^{iv}$, $R^v$ and Ar have the same meaning as above.

DESCRIPTION OF SPECIFIC EMBODIMENTS

The compounds of this invention are represented by Formula VI

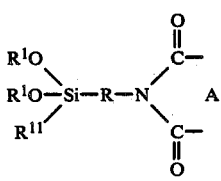

Formula VI wherein A is

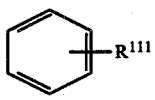

or

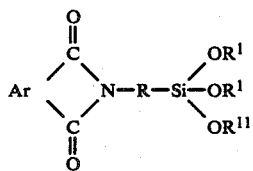

The reaction of the amino-functional silane with the anhydrides of Formula II or III yields an intermediate amic acid; while the reaction of the amino-functional silane with the esters of Formula IV or V yields an intermediate amic ester. These intermediates, when subjected to elevated temperature, are cyclized to form the corresponding imides with formation of water (in the case of the amic acid), or alcohol (in the case of the amic ester). Care must be exercised to carry out the cyclization reaction under conditions which do not cause hydrolysis or condensation of the alkoxide groups on the silicon atom, since the presence of alkoxide functional groups is essential for bonding of the silane to mineral oxide substrates and for curing the coupling agent.

Illustrative aminofunctional silanes which can be used in the synthesis of the coupling agents are:

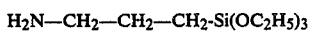

γ-aminopropyltriethoxysilane (A-1100)

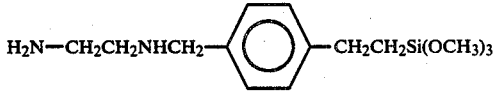

Aminoethylaminomethylphenethyltrimethoxysilane (A-0698)

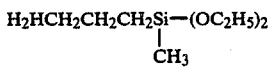

3 Aminopropylmethyldiethoxysilanes (A-0742)

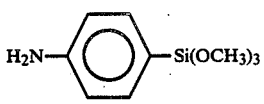

p-Aminophenyltrimethoxysilane (A-0725), (a mixture of meta (5%) and para (95%) isomers).

An overall summary of illustrative starting materials which may be used in the synthesis of the new coupling agents is shown in Table I.

TABLE I

ILLUSTRATIVE STARTING MATERIALS (SUMMARY)

| | | |
|---|---|---|
| (A-1100) | 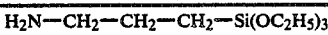 $H_2N-CH_2-CH_2-CH_2-Si(OC_2H_5)_3$ | Ia |
| (A-0698) | 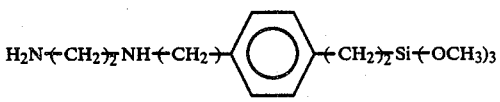 | Ib |
| (A-0725) | 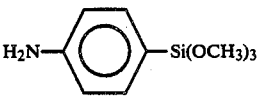 | Ic |
| (A-0742) | 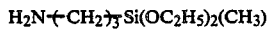 $H_2N(CH_2)_3Si(OC_2H_5)_2(CH_3)$ | Id |
| (PA) | 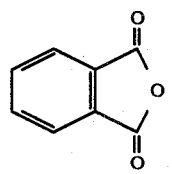 | IIa |

TABLE I-continued
ILLUSTRATIVE STARTING MATERIALS (SUMMARY)

(PMDA) — IIb (BTDA) — IIc

IId

IIe

IIf (PA) DIMETHYL ESTER — IIa$^1$ (PMDA) TETRA ETHYL ESTER — IIb$^1$ (BTDA) TETRA METHYL ESTER — IIc$^1$

The code numbers shown above and in Table I are taken from the catalog No. S-6 of Petrarch Systems, Inc., except for A-1100 which is a trade designation of Union Carbide. In the examples set forth below, all the silanes were distilled before use; the silane A-0725 required double distillation.

Illustrative anhydrides include (IIa), benzene-1,2-dicarboxylic anhydride (PA), (IIb), benzene-1,2,4,5-tetracarboxylic dianhydride (PMDA) and (IIc), benzophenonetetracarboxylic dianhydride (BTDA). In the examples set forth below, the anhydrides were either vacuum sublimed or recrystallized from acetic anhydride, and dried in a vacuum oven at 150° C. before use. Also, in the examples set forth below, the solvents, tetrahydrofuran (THF) and triethylamine (TEA), were dried and purified prior to use.

The compounds of this invention are prepared by reacting the silane with the anhydride or ester reactant. A solvent is employed when the reactant is in the form of a solid rather than a liquid. Representative suitable solvents include tetrahydrofuran, dioxane, acetonitrile, diglyme, NMP or the like. It is preferred to effect the reaction at room temperature or a lower temperature in order to minimize the possibility of premature cyclization of amic acid and consequent hydrolysis or condensation of the alkoxide functional groups. In some instances, elevated temperatures are required to effect the desired reaction to form the amic acid or amic ester. However, the reaction temperature should be maintained below about 100° C., preferably below about 90° C. The amic acid or amic acid ester formed in the first step of the reaction is then cyclized to form the corresponding imide in the second step of the reaction by heating, but without condensing the alkoxy groups. Generally, cyclization is carried out at a temperature between about 150° C. and 300° C., preferably between about 180° C. and 250° C.

In forming a composite of a mineral oxide or metal substrate bonded to a polyimide with the compositions of this invention, the mineral oxide or metal surface is first cleaned such as with an oxygen plasma or with hydrogen peroxide and ammonium hydroxide. Representative suitable mineral oxides or metals include silica, alumina, borosilicates, silicon, aluminum or the like. In one aspect of this invention, it has been found that treatment of the mineral oxide surface with ammonia subsequent to cleaning greatly improves adherence of the adhesion promoter of this invention to the mineral oxide substrate. The adhesion promoter of this invention, either (a) in the imide form or (b) in the amic acid or amic acid ester form, is applied to at least a portion of the mineral oxide substrate. The adhesion promoter is heated on the substrate to a temperature between about 100° C. and 150° C. for about 5 to 60 minutes to effect bonding to the substrate through the reactive alkoxy groups. A solution of the polyimide or its precursor then is applied to the adhesive surface and heated to a temperature between about 300° C. and 350° C. for about 30 to 120 minutes to effect bonding. Higher temperature and longer curing times can be employed.

DETAILED DESCRIPTION

Representative useful polyimides are of the type prepared from the anhydride of pyromellitic acid and 4,4'diaminodiphenyl ether. The polyimide preferably has the formula

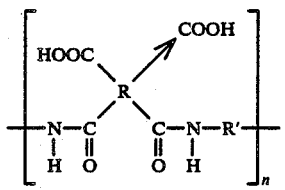

where the arrows denote isomerism, R is an organic tetravalent radical containing at least two carbon atoms, no more than 2 carbonyl groups of each polyamide-acid unit being attached to any one carbon atom of said tetravalent radical; R' is a divalent radical containing at least two carbon atoms, the amide groups of adjacent polyamic-acid units each attached to separate carbon atoms of divalent radical, and n is a positive interger sufficient to provide the polyamic acid with an inherent viscosity of at least 0.1. A preferred polyimide is Kapton (Registered Trademark) which is a polyimide formed from pyromellitic dianhydride and a diamine of the following formulae:

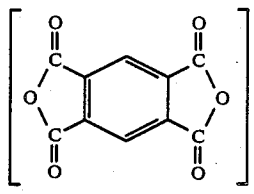

dianhydride

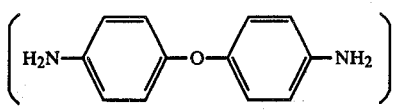

diamine and having the general formula:

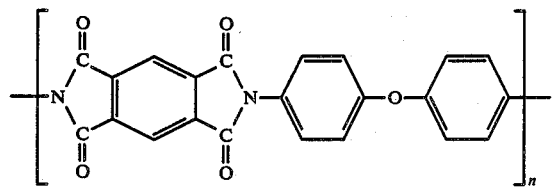

where n is an integer ranging from 150 to 650, and which has an average molecular weight ranging from 60,000 to 250,000. The above polyimides and their preparation are described in U.S. Pat. No. 3,197,614 to Edwards, which disclosure is incorporated by reference into the present application.

The examples which follow illustrate the present invention and are not intended to limit the same.

The starting materials, which have been discussed above, are shown in Table I with the code names used in the examples below.

Coupling Agents Prepared from A-1100, A-0725 and A-0742 (see Table I)

EXAMPLE 1

(CA-9)

In a three-necked flask 1.94 g of dimethylphthalate and 2.214 g of gamma-aminopropyltriethoxysilane (A-1100) were heated with stirring at 130°–135° C. in a stream of nitrogen gas. After about six hours, the reaction mixture was cooled, and the viscous orange liquid was isolated in quantitative yield. The amic ester was soluble in tetrahydrofuran (THF), isopropyl alcohol, acetone, etc. The IR spectrum of the compound shows absorptions at 1780, 1710, 1390 and 720 cm$^{-1}$, characteristic of the imide group and also a broad absorption around 1120-1240 cm$^{-1}$ corresponding to the Si-alkoxy group. The elemental analysis of the compound is given below.

|    | Found | Calculated |
|----|-------|------------|
| C% | 57.60 | 58.11 |
| H% | 6.98  | 7.12  |
| N% | 4.03  | 3.99  |

EXAMPLE 2

(CA-10)

To a mixture of 2.18 g of purified pyromellitic dianhydride (PMDA) in 20 ml of THF was added a solution containing 4.43 g of silane (A-1100) in 40 ml of THF with stirring at room temperature. During the course of the addition, the solution became homogeneous and the solution was stirred for an additional five hours at room temperature. A pale brown solid was obtained in good yield after removing the solvent under vacuum.

The IR spectrum of the amic acid showed broad absorption around 3400–3200 cm$^{-1}$ (—OH, —NH—), 1705 cm$^{-1}$ (COOH), 1650 cm$^{-1}$ (—CONH—), 1120–1040 cm$^{-1}$ (Si-alkoxy group) confirming the structure.

The elemental analysis of the compound is shown below.

|    | Found | Calculated |
|----|-------|------------|
| C% | 50.03 | 50.91 |
| H% | 7.19  | 7.27  |
| N% | 4.49  | 4.24  |

EXAMPLE 3

(CA-10a)

The compound (CA-10a) was prepared in the amic-ester form from the tetraethyl ester of pyromellitic acid. 1.83 g of tetraethylpyromellilate were heated with 2.21 g of silane (A-1100) with stirring at 85°–95° C. in a slow stream of nitrogen. After twelve hours, the reaction mixture was cooled. A red viscous liquid was obtained in nearly quantitative yield.

The IR spectrum of the compound showed absorptions at 3250 cm$^{-1}$ (—NH—), 1720 cm$^{-1}$ (-ester), 1640 cm$^{-1}$ (—CONH—), 1120–1050 cm$^{-1}$ (Si-alkoxy) confirming the amic-ester structure.

EXAMPLE 4

(CA-11)

To a mixture of 3.22 g benzophenone-tetracarboxylic dianhydride (BTDA) in 30 ml of THF, was added a solution of 4.43 g of A-1100 in 50 ml of THF at room temperature with stirring. The solution became homogeneous during the course of addition. The solution was stirred for an additional five hours. A white solid was obtained in quantitative yield after removing the solvent under vacuum.

The IR spectrum of the compound showed broad absorptions around 3450–3250 cm$^{-1}$ (—OH, —NH—), 1710 cm$^{-1}$ (COOH), 1660–1640 cm$^{-1}$ (—CO—, CONH—) and a broad absorption around 1120–1040 cm$^{-1}$ (Si-alkoxy), confirming the structure. The elemental analysis of the compound is shown below.

|    | Found | Calculated |
|----|-------|------------|
| C% | 54.60 | 54.97 |
| H% | 6.73  | 6.81  |
| N% | 3.71  | 3.66  |

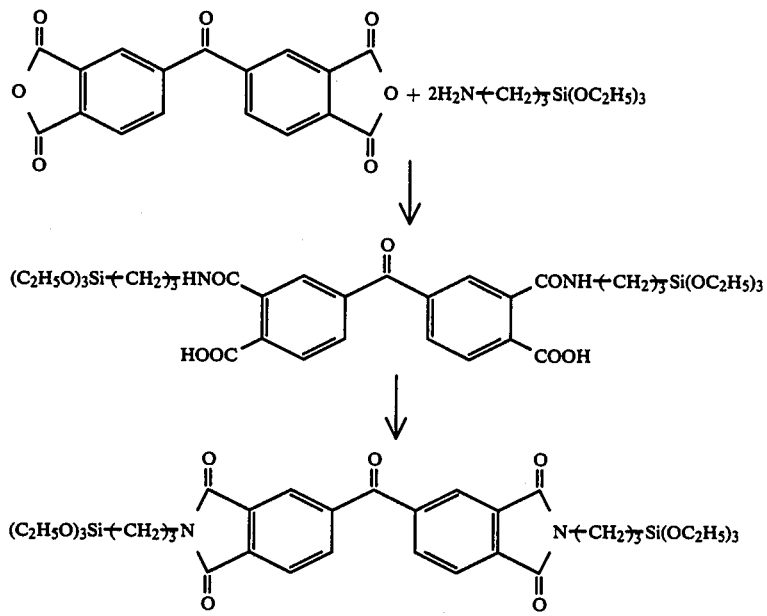

Synthesis of CA-11 (Example 4)

EXAMPLE 5

(CA-11a)

A mixture of 2.07 g of tetramethyl benzophenonetetracarboxylate was heated with 2.21 g of (A-1100) without any solvent at 85°–95° C. in a slow stream of nitrogen. After 12 hours, a viscous liquid, red in color, was isolated in good yield.

The IR spectrum of the compound has absorptions around 3360–3250 cm$^{-1}$ (—HN—), 1720 cm$^{-1}$ (ester), 1660–1640 cm$^{-1}$ (—CO—, CONH) and a broad absorption around 1120–1040 cm$^{-1}$ (Si-alkoxy).

EXAMPLE 6

(CA-15)

Sublimed phthalic anhydride (1.48 g) in 20 ml of THF was placed in a three-necked flask equipped with a magnetic stirrer, dropping funnel, nitrogen inlet and drying tube. To this solution, 2.13 g of silane A-0725 in 30 ml of THF was added slowly. The solution was stirred for four hours under nitrogen and then the solvent was removed under reduced pressure at room temperature. The product was light yellow in color and was obtained in quantitative yield.

EXAMPLE 7

(CA-16)

Purified phthalic anhydride (1.48 g) in 20 ml of THF was placed in a three-necked flask equipped with the accessories mentioned in the preceding example. The silane A-0742 (1.91 g) in 30 ml of THF was added slowly under nitrogen. Stirring was continued at room temperature for four hours, and the coupling agent was then isolated in quantitative yield by removing the solvent under reduced pressure. The product is a low-melting, waxy, colorless solid.

EXAMPLE 8

(CA-17)

A 2.18 gm of PMDA was placed with 20 ml of THF in a three-necked flask equipped with the accessories mentioned above. The silane A-0725 (4.27 g in 40 ml of THF) was added dropwise. During the addition, the solution became more homogeneous and after 20 minutes, it was clear. The solution was then stirred at room temperature for four hours. The product was obtained in quantitative yield as a yellow solid after removing the solvent under reduced pressure.

EXAMPLE 9

(CA-18)

2.18 g of PMDA was placed with 20 ml of THF in a three-necked flask equipped as described above. 3.83 g of silane A-0742 in 40 ml of THF was added dropwise with stirring. The solution became clear during the course of addition. It was then stirred at room temperature for four hours and then the solvent was evaporated under reduced pressure. The coupling agent was obtained in quantitative yield as a colorless, viscous fluid.

EXAMPLE 10

(CA-19)

The BTDA (3.22 g in 30 ml of THF) was placed in a three-necked flask equipped with accessories as described above. To this solution, 4.27 g of silane A-0725 in 40 ml THF was added slowly at room temperature under nitrogen. The solution became clear after about 20 minutes, and it was then stirred at room temperature for about four hours. The solvent was evaporated under reduced pressure to yield a pale yellow solid in quantitative yield.

EXAMPLE 11

(CA-20)

3.22 g of BTDA in 30 ml of THF was placed in a three-necked flask equipped with the accessories described above. To this solution, 3.83 g of silane A-0742 in 40 ml of THF was added slowly at room temperature under nitrogen. The solution became homogeneous in about 30 minutes and stirring was continued for another four hours. The solution was then evaporated under vacuum, and the coupling agent was obtained as a colorless waxy solid in quantitative yield.

EXAMPLE 12

(CA-21)

The acid chloride (2-carbomethoxybenzoyl chloride) prepared from 1.8 g of methyl phthalate was used for this reaction. The acid chloride in 20 ml of THF was placed in a three-necked flask equipped with the accessories described above. To this, a solution of 2.13 g of silane A-0725, 1 ml of triethylamine and 30 ml of THF was added dropwise while cooling in an ice bath. The reaction mixture was stirred with cooling for an hour, and then at room temperature for about three hours. The mixture was then filtered to remove the precipitated amine hydrochloride and the filtrate was evaporated under reduced pressure. The product was pale yellow in color, and was obtained in quantitative yield.

EXAMPLE 13

(CA-22)

The acid chloride, 2-carbomethoxybenzoyl chloride, obtained from 1.8 g of the corresponding acid, with 20 ml of THF was placed in a three-necked flask equipped with the accessories described above. A solution of 1.91 g of silane A-0742, 1 ml of triethyl amine and 2 ml of THF was added slowly to the ice cold solution of acid chloride. The reaction mixture was stirred with cooling for an additional hour, and then at room temperature for three hours. The mixture was filtered to remove the amine-hydrochloride, and the filtrate was evaporated under reduced pressure. The product was obtained in quantitative yield as a pale yellow, viscous fluid.

EXAMPLE 14

(CA-23)

A 3.19 g of 2,5-dicarbomethoxyterephthaloyl chloride in 30 ml of THF was placed in a three-necked flask equipped with the accessories described above. To this, a solution of 4.27 g of silane A-0725, and 2 ml of triethylamine, in 40 ml of THF was added slowly with cooling in an ice bath. The reaction mixture was stirred with cooling for an hour, and at room temperature for four hours. It was then filtered to remove the amine hydrochloride, and the solvent was removed from the filtrate under reduced pressure. The coupling agent was obtained in quantitative yield as a yellow solid.

EXAMPLE 15

(CA-24)

3.19 g of 2,5-dicarbomethoxyterephthaloyl chloride in 30 ml of THF was placed in a three-necked flask equipped with the accessories described above. To this solution, cooled in an ice bath, a solution of 3.83 g of silane A-0742 and 2 ml of triethyl amine in 40 ml of THF was added slowly. The reaction mixture was stirred for an hour with cooling and then for four hours at room temperature. It was then filtered to remove the amine-hydrochloride, and the filtrate was evaporated under reduced pressure. The product was obtained in quantitative yield as a pale yellow solid.

EXAMPLE 16

(CA-25)

The diacid dichloride, 4,4'-carbonyldi-2-carbomethoxybenzoyl chloride, obtained from 3.86 g of the corresponding diacid diester, was placed with 30 ml of THF in a three-necked flask equipped with the accessories described above. To this solution, cooled in an ice bath, a solution of 4.27 g of silane A-0725 and 2 ml of triethylamine in 40 ml of THF was added slowly. The reaction mixture was stirred for one hour under ice cold conditions and then at room temperature for four hours. It was then filtered to remove the salt and the filtrate was evaporated under reduced pressure. The product, a yellow solid, was obtained in quantitative yield.

EXAMPLE 17

(CA-26)

The diacid dichloride, 4,4'-carbonyldi-2-carbomethoxybenzoyl chloride, obtained from 3.86 g of the corresponding diacid diester was placed with 30 ml of THF in a three-necked flask equipped with the accessories described previously. To this solution cooled in an ice bath, a solution of 3.83 g of silane A-0742, 2 ml of triethylamine and 40 ml of THF was added slowly. The reaction mixture was stirred with cooling for an hour and then at room temperature for four hours. The reaction mixture was filtered to remove the salt, and the filtrate was evaporated under reduced pressure. The product, a yellow waxy solid, was obtained in quantitative yield.

EXAMPLE 18

(CA-10b)

3.19 g of 2,5-dicarbomethoxyterephthaloyl chloride was placed in 30 ml of THF in a three-necked flask equipped with the accessories described above. To this solution, cooled in an ice bath, 4.43 g of silane A-1100, 2 ml of triethylamine and 40 ml of THF were added slowly. The mixture was stirred with cooling for an hour, and then at room temperature for four hours. It was then filtered to remove the precipitated amine-hydrochloride, and the filtrate was distilled under reduced pressure. The product, a pale yellow solid, was obtained in quantitative yield.

EXAMPLE 19

(CA-11b)

The diacid dichloride, 4,4-carbonyldi-2-carbomethoxybenzoyl chloride, derived from 3.86 gm of the diacid was placed in 30 ml of THF in a three-necked flask equipped with the accessories described above. To this solution, cooled in an ice bath, a solution of 4.43 g of silane A-1100, 2 ml of triethylamine, and 40 ml of THF was added slowly. The reaction mixture was stirred with cooling for an hour, and then at room temperature for four fours. The reaction mixture was filtered to remove the salt, and the filtrate was evaporated under reduced pressure. The product, pale yellow in color, was obtained in quantitative yield.

Coupling Agents Prepared from A-0698 (Ib in Table I)

EXAMPLE 20

(CA-12)

In a three-necked flask, 1.94 g of dimethyl phthalate and 3.32 g of A-0698 were heated with stirring at 125°–35° C. in a slow streamm of nitrogen. After twelve hours, the reaction mixture was cooled; and a viscous liquid, red in color, was obtained in good yield.

The IR spectrum of the compound showed absorptions at 1780, 1710, 1390 and 720 cm$^{-1}$ (imide) and a broad absorption around 1120–1060 cm$^{-1}$ (Si-alkoxy) characteristic of the compound.

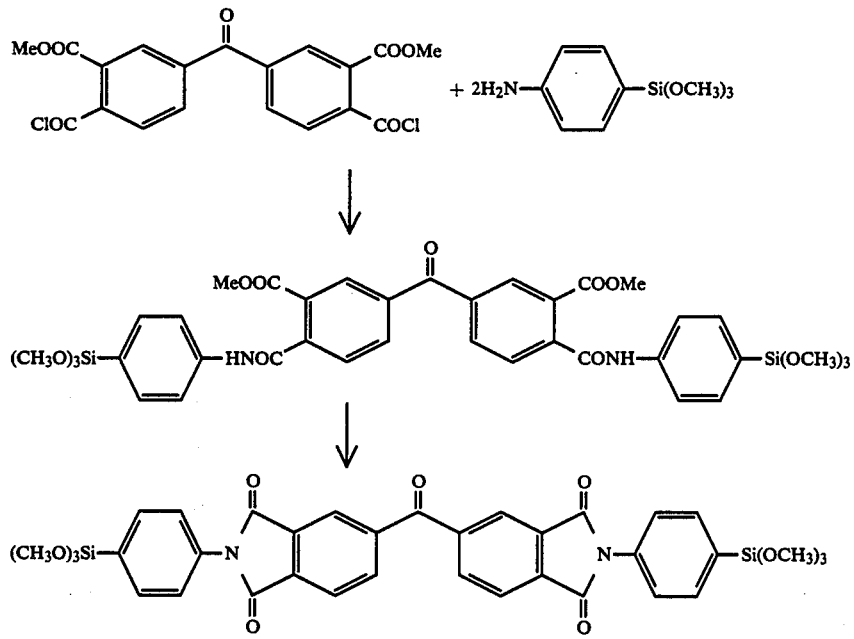

Synthesis of CA-25 (Example 16)

EXAMPLE 21

(CA-13)

To a solution containing 2.18 g of purified PMDA in 20 ml of THF, a solution of 6.63 g of A-0698 in 70 ml of THF was added slowly with stirring. The solution became homogeneous for a while, and then a solid precipitated. After stirring for an additional five hours, the solid was isolated by filtration in about 90% yield.

The IR spectrum of the compound showed broad absorptions around 3400–3200 $cm^{-1}$, 1660–1580 $cm^{-1}$ and 1100–1040 $cm^{-1}$ (Si-alkoxy). The explanation for the broad peak in the carbonyl region is that the compound may exist as a zwitterion of the secondary amino group of the silane moiety with carboxyl group. This may also explain the precipitation of solids from the reaction medium. The synthesis of the corresponding amic ester compound was carried out in order to avoid the formation of the ion pair.

EXAMPLE 22

(CA-13a)

In a three-necked flask, 1.83 g of tetraethylpyromellitate and 3.32 g of A-0698 was heated with stirring at 100°–110° C. in a slow stream of nitrogen. After twelve hours, a viscous liquid, red in color was obtained in quantitative yield.

The IR spectrum of the compound has absorptions at 3300–3200 $cm^{-1}$ (—NH—), 1720 $cm^{-1}$ (ester), 1650 $cm^{-1}$ (—CONH—) and 1120–1040 $cm^{-1}$ (Si-alkoxy) confirming the amic-ester structure.

EXAMPLE 23

(CA-14)

To a solution containing 3.22 g of BTDA in 30 ml of THF, a solution of 6.63 g of A-0698 in 70 ml of THF was added with stirring at room temperature. The solution became homogenous for a while and then solids precipitated out from the reaction medium. The solids were isolated by filtration in 80% yield.

The IR spectrum of the compound showed broad absorptions around 3400–3200, 1670–1560 and 1100–1060 $cm^{-1}$. As in the case of CA-13, this is attributed to ion pair formation.

EXAMPLE 24

(CA-14a)

2.07 g of the tetramethylbenzophenonetetracarboxylate and 3.3 g of A-0698 were heated with stirring at 100°–110° C. in a slow stream of nitrogen. After 12 hours, the product, a brown viscous fluid was isolated in quantitative yield.

The IR spectrum of the compound showed absorptions at 3300–3250 $cm^{-1}$ (—NH—), 1720 $cm^{-1}$ (ester), 1660–1640 $cm^{-1}$ (—CO—, —CONH—) and 1120–1040 $cm^{-1}$ (Si-alkoxy) confirming the structure.

EXAMPLE 25

CYCLIZATION OF THE COUPLING AGENTS DESCRIBED IN EXAMPLES 1–5 AND THEIR HYDROLYSATES

The conditions for the cyclization (imide formation) of the above amic acid and amic ester intermediates were studied in a differential scanning calorimeter (DSC) and by determining the weight loss curves in thermogravimetric analysis (TGA). These studies were carried out with a du Pont 910 DSC and with a du Pont 951 TGA instrument equipped with du Pont 1090 Thermal Analyser accessory. DSC measurements were done at a heating rate of 10° C./minute and TGA measurements were done at a heating rate of 20° C./minute, both in nitrogen atmosphere.

The hydrolysis of the alkoxy groups for the study of thermal stability of cured hydrolyzates was carried out as follows: One grsam of the amic acid or amic ester intermediate compound was dissolved in 10 ml of THF and distilled water was added to this solution until it became hazy. The solution was stirred for five hours at room temperature. The product was obtained after removing the solvent under vacuum. The thermal studies were carried out within four to six hours.

CA-9 (Product of Example 1)

DSC analysis of the hydrolysate of CA-9 shows four endothermic absorptions, the predominant one occurring at 104° C. This shows that condensation of the silanol groups, which form in the hydrolysis of the alkoxy groups, takes place below 120° C.

CA-10 (Product of Example 2)

DSC analysis of CA-10 shows that cyclization to imide begins at 142° C., with the maximum absorption around 170° C. The IR spectrum of the residue, obtained from DSC measurements, shows the following absorptions: 1770, 1710, 1390 and 720 $cm^{-1}$ (imide) and 1120–1020 $cm^{-1}$, confirming the imide structure.

CA-10a (Product of Example 3)

DSC analysis of the compound CA-10a shows a broad endothermic absorption with a maximum at 232° C. and has a maximum weight loss (from TGA) around 239° C. This suggests that cyclization occurs at a higher temperature for the amic ester than for the corresponding amic-acid (CA-10) compound.

CA-11 (Product of Example 4)

DSC analysis of the compound CA-11 has a broad absorption starting at 147° C. and the maximum occurs at 175° C. The IR spectrum of the cyclised compound shows characteristic absorptions at 1775, 1705, 1690, 1390, 725 $cm^{-1}$ (imide) and a broad peak at 1100–1050 $cm^{-1}$ (Si-alkoxy).

DSC analysis of the hydrolysate of CA-11 has two broad endothermic absorptions with maxima at about 90° C. and 193° C. The absorption at lower temperature corresponds to silanol condensation, and that at higher temperature to cyclization. The cyclization maximum occurs at higher temperature than in the case of unhydrolyzed imide because of the crosslinked structure of the silanol condensation product.

CA-11a (Product of Example 5)

DSC analysis of compound CA-11a does not show a significant endothermic absorption in any temperature range; but the maximum weight loss in the TGA occurs at about 320° C. This shows that cyclization takes place at a higher temperature for this amic ester intermediate than in the case of CA-10 and CA-10a.

EXAMPLE 26

THERMAL RESPONSE OF CURED HYDROLYSATES

The curing of the hydrolyzed products was done in two stages: initially, at 110° C. under vacuum overnight and then, at 180°–185° C. for two hours. As a practical matter, these curing conditions are suitable for the application of the coupling agents of the present invention. The IR spectrum of the post-cured hydrolysates shows the characteristic imide and siloxane absorptions, and also medium absorption at about 3000–2900 cm$^{-1}$ corresponding to C-H stretching. The dynamic thermal stability, weight residue at 850° C. and isothermal stability (in terms of weight loss) in a nitrogen atmosphere are summarized for selected compounds in Table II with reference to the cured hydrolyzate of a commercial coupling agent (A-1100).

TABLE II

THERMAL PROPERTIES OF CURED HYDROLYSATES

| Code No. | Dynamic Onset of Decomposition (°C.) | Weight Residue at 850° C. (%) | Isothermal Weight Loss After Two Hours at 425° C. | 450° C. |
|---|---|---|---|---|
| A-1100 | 400 | 66 | 22 | — |
| CA-9 | 487 | 38 | 22.5 | 39 |
| CA-10 | 503 | 66 | 8 | 15 |
| CA-11 | 512 | 61 | 7 | 20 |
| CA-25 | 545 | 70 | — | 5 |

The cured hydrolysate of CA-9 shows onset of decomposition at 487° C., much higher than for A-1100 (400° C.); but the isothermal stability at 425° C. is comparable for A-1100 and CA-9. This observation reflects the higher siloxane content of the hydrolysate of the A-1100 compound; and the large difference in the weight residue at 850° C. for the cured hydrolysates of the two compounds may be similarly explained. The cured hydrolysates of compounds CA-10 and CA-11 have decomposition temperatures above 500° C. and exhibit less than 10% and 20% isothermal weight loss after two hours at temperatures of 425° and 450° C. respectively. The thermal stability of CA-25 is even higher. The data generally reflect the outstanding thermal stability of the new coupling agents. Thermal response data for selected coupling agents prepared from A-0698 are shown in Table III.

TABLE III

| Coupling Agent | Onset of Decomposition (°C.) | Weight Residues at 850° C. (%) |
|---|---|---|
| A-0698 | 389 | 55 |
| CA-12 | 385 | 46 |
| CA-13 | 440$^a$ | 61 |
| CA-14 | 450$^a$ | 69 |

$^a$The values given above correspond to a 10% weight loss

The cured hydrolysates of CA-12 and of A-0698 have similar apparent thermal stability. In this case, the introduction of the imide group does not improve thermal response in TGA. Thermal degradation seemingly begins somewhere other than in the imide group, probably in the side chain; and the new compound has a thermal response which is similar to that of the parent silane. However, the cured hydrolysates of CA-13 and CA-14 have excellent thermal stability compared to that of A-0698, and the weight loss occurs over a range of temperature. This may be attributed to incomplete cyclization of the ionic structure; and complete cyclization may require a pH corresponding to the isoelectric point for the hydrolyzed product. This phenomenon may play a significant role in improving thermal stability, when controlling the pH of the solution used for application.

A summary of TGA data on cured hydrolysates from Silane A-1100, Silane A-0698 and the coupling agents described in Examples 1 to 10 is presented in Table IV.

TABLE IV

THERMAL STABILITY OF CURED (2 hrs/180° C.–185° C.) HYDROLYSATES PRODUCTS OF EXAMPLES 1–5 AND 20–24

| Compound | Synthesis Starting Materials shown in Table I (Silane) | | TGA in N$_2$ | |
|---|---|---|---|---|
| | | | Onset of Decomposition (°C.) | Residue at 850° C. (%) |
| A-1100 | Ia | — | 400 | 66 |
| A-0698 | Ib | — | 389 | 55 |
| CA-9 | Ia | IIa′ | 487 | 38 |
| CA-10 | Ia | IIb | 503 | 66 |
| CA-10a | Ia | IIb′ | 275 | 38 |
| CA-11 | Ia | IIc | 512 | 61 |
| CA-11a | Ia | IIc′ | 287 | 43 |
| CA-12 | Ib | IIa′ | 385 | 46 |
| CA-13 | Ib | IIb | 440* | 61 |
| CA-13a | Ib | IIb′ | 410* | 58 |
| CA-14 | Ib | IIc | 450 | 67 |
| CA-14a | Ib | IIc′ | 309* | 64 |

*Values are temperatures corresponding to 10% wt. loss

EXAMPLE 27

EVALUATION OF COUPLING EFFECTIVENESS

The coupling agents prepared as described in Examples 1 to 24 may be evaluated for effectiveness as adhesion promoters for polyimides by procedures known in the art which are summarized below. Specific conditions may be modified, depending on the solubility of the compound, and on other properties related to chemical structure. The examples which follow show results obtained in the evaluation of coupling effectiveness and thermal stability for the new compounds CA-11 and CA-25 on several substrates. It must be understood that other compounds, other substrates and other application conditions are within the scope of the present invention, and that the examples which follow are merely illustrative of the excellent results which can be obtained with the new compounds.

Preparation of Peel Test Samples and Measurement of Peel Strengths (A) Substrate Preparation and Application of Silane The substrates were cleaned by an oxygen plasma (e.g., power, 100 W; pressure, 60 m torr; 2 min.) or by chemical treatment (e.g., a 5/1/1 solution of distilled water/hydrogen peroxide/ammunium hydroxide, 15 min. at 90° C.) A solution of coupling agent (e.g., A-1100 in water; CA-11, CA-25 in a water/tetrahydrofuran (THF) mixture was spun onto the substrate (e.g., borosilicate glass, silicon oxide glass or silicon water) at 5000 rpm for 30 seconds. Prior to application of the polyimide, the silane-treated substrate was heated at moderate temperature, typically 10 min. at 110° C.

(B) Application of Polyimide

A solution of polyimide (du Pont Pyralin 5878) was spun onto the silane primed substrate at 4000 rpm for 30 sec., and baked at 130° C. for 10 min. The process was repeated as needed to obtain the desired film thickness. The thickness of the film has an important effect on the values obtained for adhesion. Final curing of the polyimide film was for 30 min. at 350° C. in air or in nitrogen (unless otherwise indicated).

(C) Adhesion

Adhesion was determined by a 90° peel test on 5 mm wide strips at a rate of 5 mm/min., as described in the standard method ASTM D-903 (1978). Results are reported in grams/cm.

EXAMPLE 28

This example shows the results obtained in the comparative evaluation of a commercial coupling agent (A-1100) and a compound of the present invention (CA-11) on several substrates, using the same concentration of coupling agent (0.1%), the same polyimide. Results are summarized in Table V. Since the peel strength increases with increasing thickness of the polyimide film, this parameter should be taken into account when the numerical values of peel strength are compared.

EXAMPLE 29

Results obtained in an experiment where the polyimide films were cured in a nitrogen atmosphere are shown in Table VI. The substrate was a silicon wafer cleaned by an oxygen plasma. The commercial coupling agent A-1100 was applied from a 0.1% aqueous solution while the compound CA-25 was applied from a 0.5% solution in 95/5 THF/H$_2$O where the apparent pH was adjusted to 3.0 with HCl, and the solution was aged at room temperature for 8 hours prior to application.

50% can be obtained when the application conditions for CA-25 are modified.

EXAMPLE 30

Improvement in peel strength obtained by exposing the substrate primed with CA-25 to ammonia vapor prior to curing. A 0.5% solution of CA-25 in 95/5 dioxane/water was adjusted to an apparent pH of 3.0 with HCl, and aged for 8 hours as described above in Example 29. It was applied to a silicon wafer by spin casting, and the primed wafer was stored for 14 hours in a closed container where a Petri dish containing about 200 ml of commercial NH$_4$OH was also placed. It was then cured, and the polyimide was applied and cured as described in Example 29. For polyimide film thickness of 13.2–13.3 μm, the peel strength was increased from 445 g/cm (Table VI) to a value of 680 g/cm for the example exposed to NH$_3$ vapor prior to casting of the polyimide film. This value is essentially the same as obtained for the same polyimide thickness when A-1100 is used as the adhesion promoter (Table VI).

TABLE VI

| Thickness of polyimide film (μm) | Peel Strengths (g/cm) | |
|---|---|---|
| | CA-25 | A-1100 |
| 7.0~7.3 | 350 | 460 |
| 10.0~10.4 | 390 | 600 |
| 13.2~13.3 | 445 | 700 |
| 14.0~14.1 | 540 | 800 |

EXAMPLE 31

The thermal response of the adhesive bond obtained

TABLE V

| Conditions Substrate | Conditions for Coupling Agents Solutions | | Curing conditions for Coupling Agents | Curing conditions for Polyimides | Peel Strengths* (g/cm) | |
|---|---|---|---|---|---|---|
| | CA-11 | A-1100 | | | CA-11 | A-1100 |
| Borosilicate | 0.1 wt % solution in 95/5 THF/H$_2$O volumetric ratio, aged 2 hrs at RT | 0.1 V % solution in 100% H$_2$O, aged 2 hrs at RT | 180° C. 2 hrs in air | 350° C. 30 min in air | 100 | 60 |
| Silicon Oxide | 0.1 wt % solution in 95/5 THF/H$_2$O volumetric ratio, aged 2 hrs at RT | 0.1 V % solution in 100% H$_2$O, aged 2 hrs at RT | 180° C. 2 hrs in air | 350° C. 30 min in air | 170 | 120 |
| Silicon | 0.1 wt % solution in 95/5 THF/H$_2$O volumetric ratio, aged 30 min. | 0.1 V % solution in 100% H$_2$O, aged 30 min at RT | 110° C. 10 min in air | 350° C. 30 min in air | 320 | 310 |

*Film thickness:
4.0~4.5 μm for borosilicate glass
3.5~4.0 μm for silicon oxide
6.0~7.5 μm for silicon Before application of the polyimide, the substrate treated with coupling agent was cured in each case for 10 min. at 110° C. The spin-cast polyimide film was cured for 30 minutes at 350° C. in a nitrogen atmosphere. It is evident from the results shown in Table VI that the conditions used for application of CA-25 gave results which were somewhat inferior to those obtained for A-1100 applied as recommended by the manufacturer. However, the experiment described in Example 30 shows that an improvement in peel strength of about with CA-11 was evaluated by measuring peel strength on oxygen plasma cleaned silicon wafers after heat treatment of the composite at 400° C. in air and in nitrogen for specified times. The results obtained are shown in Table VII.

EXAMPLE 32

The retention of peel strength after prolonged exposure to 400° C. of samples in which 0.5% CA-25 was used in place of 0.1% CA-11 is compared with that obtained with A-1100 in Table VIII. It is evident from these results that not only is the thermal stability of the bond even greater for CA-25 than for CA-11 but that, for this particular coupling agent, excellent peel strength can be retained after several hours at 400° C. in air, a condition of thermal exposure which destroys the adhesive bond for most known systems where silane coupling agents are used. In nitrogen, the peel strength value for CA-25 is essentially unchanged after 4 hours at 400° C.

EXAMPLE 33

The ester-acid chlorides (IId, IIe and IIf in Table I) were prepared from the respective anhydrides as follows:

2-Carbomethoxybenzoylchloride (IId)

Phthalic anhydride (7.4 g) and absolute methanol (5.0 ml) were refluxed for about 2 hours. Excess methanol was distilled off, and 10 ml of dry benzene was added. The distillation was continued and the hot viscous liquid residue was filtered immediately. The white crystals which separated out on cooling were recrystallized from a benzene-hexane mixture. Yield: 7.5 g; m.p. 81° C. (lit. 83° C.).

A mixture (9.0 g) of the above compound and 25 ml of thionyl chloride was refluxed for one hour at 90° C., and the excess thionyl chloride was removed under reduced pressure.

TABLE VII

| Heat Treatment | Peel Strength (g/cm) | | | |
|---|---|---|---|---|
| | Air Atmosphere | | Nitrogen Atmosphere | |
| Time at 400° C. | CA-11 | A-1100 | CA-11 | A-1100 |
| 0 min | 425* | 425* | 800 | 800 |
| 10 min | 240 | 220 | — | — |
| 20 min | 210 | 200 | — | — |
| 1.0 hr | 170 | 160 | 700 | 700 |
| 2.0 hr | 120 | 120 | — | — |
| 2.5 hr | — | — | 650 | 650 |
| 3.0 hr | 80 | — | — | — |
| 4.0 hr | — | — | 650 | 600 |

*Calculated peel strengths after considering the effect of thickness of film.
Film thickness:
5.5 μm for tests in air
14.0 μm for tests in nitrogen
Conditions for applying coupling agents:
0.1 wt % solution in 95/5 THF/water for CA-11, and 0.1 wt % solution in 100% water for A-1100, aged 30 min., cured 10 min at 110° C.
Curing condition for Polyimide: 350° C., 30 min under nitrogen.

TABLE VIII

| Heat Treatment | Peel Strength Retained (%) | | | |
|---|---|---|---|---|
| | Air Atmosphere | | Nitrogen Atmosphere | |
| Time at 400° C. | CA-25 | A-1100 | CA-25 | A-1100 |
| 0 | 100 | 100 | 100 | 100 |
| 1 | 62 | 38 | 99 | 88 |
| 2 | 52 | 28 | 95 | — |
| 2.5 | — | — | — | 81 |
| 3 | 50 | — | 97 | — |
| 4 | 41 | — | 99 | 75 |

Dry benzene (three 10 ml portions) was then added and the solution benzene (three 10 ml portions) was then added and the solution was distilled in vacuo to remove any residual unreacted thionyl chloride. The crude acid chloride was used immediately for reaction with the silane.

2,5-Dicarbomethoxyterephthaloyl chloride (IIc)

PMDA (27.25 g) was added to 250 ml of dry methanol, and the mixture was refluxed until the anhydride had dissolved (about 2 hrs.). The clear solution was concentrated to approximately 125 ml, and allowed to stand at room temperature for a day. A white solid precipitated out and was isolated by filtration and recrystallized from methanol. Yield: 25 g; m.p. 234° C. (lit. 238° C.).

10 grams of the diacid-diester was added to 30 ml of thionyl chloride, and refluxed at 95°–100° C. for about 5 hours, until all the solid had dissolved. The excess thionyl chloride was then removed under reduced pressure, and the white solid obtained was recrystallized from a mixture of dry benzene and hexane. Yield: 8.7 g; m.p. 135° C. (lit. 138° C.).

4,4¹-Carbonyldi-2-carbomethoxylbenzoyl chloride (IIf)

BTDA (32.2 g) was refluxed with 60 ml of dry methanol for about 2 hours until all the solid had dissolved, and then for an additional hour. The excess methanol was removed under reduced pressure at room temperature. The yellow oil thus obtained was dried under vacuum ($10^{-2}$ torr) at room temperature overnight, to give a light yellow crystalline solid. The product was washed with hot hexane, and dried at 60° C. overnight in a vacuum oven. Yield: 30.5 g. (The product does not have a sharp melting point).

The diester-diacid chloride was obtained by refluxing 5 g of the above diester diacid with 15 ml of thionyl chloride at 95°–100° C. for five hours. The excess thionyl chloride was distilled off under reduced pressure. Dry benzene (three 10 ml portions) was added, and the solution was stripped in vacuo to remove unreacted thionyl chloride. The product was a pale yellow, low melting solid whch was used immediately for reaction with the silane.

Illustrative esters (IIa', IIb' and IIc' in Table I) are the dimethyl ester of phthalic acid, the tetramethyl and the tetraethyl esters of pyromellitic acid and of benzophenone tetracarboxylic acid. Derivatives of these anhydrides and esters can also be employed for synthesizing the coupling agents of the present invention, providing that substituents and modifying elements in the molecule do not enter into competing reactions with the primary amino group, or with the alkoxide group of the aminofunctional silane.

We claim:
1. A composite product comprising substrates selected from the group consisting of a mineral oxide and a metal adhered to a polyimide with an adhesion promoter positioned between said substrate and said polyimide, said promoter having the formula

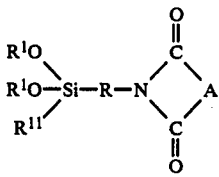

wherein A is selected from the group consisting of

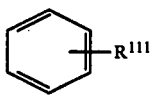

and

-continued

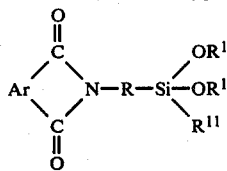

wherein R is a divalent radical having more than two carbon atoms, $R^1$ is lower alkyl from 1 to 6 carbon atoms, $R^{11}$ is $OR^1$ or lower alkyl from 1 to 6 carbon atoms, $R^{111}$ is hydrogen or lower alkyl from 1 to 6 carbon atoms and Ar is an aromatic group.

2. A composite product of claim 1 wherein R is propylene.

3. A composite product of claim 1 wherein R is ethylaminomethylphenyl ethyl.

4. A composite product of claim 1 wherein R is phenylene.

5. A composite product of claim 1 wherein A is phenylene.

6. A composite product of claim 1 wherein A is derived from phthalic anhydride.

7. A composite product of claim 1 wherein A is benzophenonetetracarboxylic dianhydride.

8. A composite product of claim 1 wherein A is derived from pyromellitic anhydride.

9. A composite product of claim 1 wherein A is derived from 4,4'-carbonyldi-2-carbomethoxybenzoyl halide.

* * * * *